US006933307B2

United States Patent
Gerusz et al.

(10) Patent No.: US 6,933,307 B2
(45) Date of Patent: Aug. 23, 2005

(54) FUNGICIDAL PHENYLIMINE DERIVATIVES

(75) Inventors: Vincent Gerusz, Lyons (FR); Darren James Mansfield, Lyons (FR); Joseph Perez, Lyons (FR); Jean-Pierre Vors, Lyons (FR)

(73) Assignee: Bayer Cropscience SA (FR)

( * ) Notice: Subject to any disclaimer, the term of this patent is extended or adjusted under 35 U.S.C. 154(b) by 479 days.

(21) Appl. No.: 09/923,198

(22) Filed: Aug. 6, 2001

(65) Prior Publication Data

US 2002/0103168 A1 Aug. 1, 2002

(30) Foreign Application Priority Data

Aug. 4, 2000 (EP) .............................. 00116819

(51) Int. Cl.[7] .......................... C07D 249/20
(52) U.S. Cl. ...................... 514/364; 548/146
(58) Field of Search .................... 548/202; 514/365

(56) References Cited

U.S. PATENT DOCUMENTS

| 4,059,590 A | 11/1977 | Moore |
| 4,389,236 A | 6/1983 | Durr |
| 4,659,360 A | 4/1987 | Baum et al. |
| 5,468,857 A | 11/1995 | Buckley et al. |

FOREIGN PATENT DOCUMENTS

| DE | 19623744 A1 | 12/1997 |
| EP | 0563384 | 10/1993 |
| GB | 1413513 | 11/1975 |
| JP | 53-113024 | 10/1978 |
| JP | 60-126267 | 7/1985 |
| WO | 99/21837 | 5/1999 |
| WO | 00/46184 | 8/2000 |

OTHER PUBLICATIONS

Patent Abstracts of Japan. European Patent Office. Publication No. 11180964; Publication date Jul. 6, 1999.

"Studies on Potential Pesticides: Part XI—Synthesis of Various Thiourea & Schiff Base Derivatives of Bis(4–aminophenyl)methane & Their Biological Activities"; A. K. Sen, et al.; *Indian J. Chem.*; vol. 18B; Oct. 1979; pp. 381–382.

"Condensation of Acetone with Amino Derivatives from Nitrofen, Chlornitrofen and Chlomethoxynil in Gas Chromatograph"; T. Yamada; *Journal of Pesticide Science*; 7 (3); Aug. 1982; pp. 373–376.

*Primary Examiner*—Joseph K. McKane
*Assistant Examiner*—Kamal Saeed
(74) *Attorney, Agent, or Firm*—Ostrolenk, Faber, Gerb & Soffen, LLP

(57) ABSTRACT

The invention provides fungicidal compounds of formula I and salts thereof:

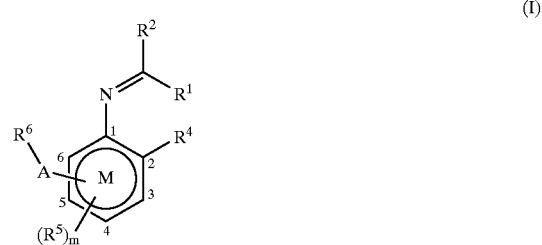

wherein
the various radicals and substituents are as defined in the description, fungicidal compositions containing them and method for combating fungi which comprises applying these.

20 Claims, No Drawings

FUNGICIDAL PHENYLIMINE DERIVATIVES

This invention relates to new fungicidal phenylimine derivatives, their process of preparation and the fungicidal compositions containing them.

WO 95/22532 relates to substituted phenyltriazolinones claimed as herbicides and discloses inter alia a compound of formula A for which there is no characterising data therein.

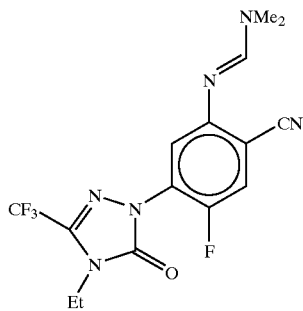

(A)

The abstract, composition claim and use claim refer only to the use of such compounds as herbicides and indeed the description supports the invention only with herbicidal activity data. There is a sentence in the specification that states that certain compounds show fungicidal activity, although no fungicidal activity data are provided. No indication is given as to which compounds are fungicidal and there is no suggestion that compound A could be fungicidal.

We have now found that certain phenylimines have fungicidal activity. Therefore, the invention provides the use of a compound of general formula (1) and salts thereof as fungicides:

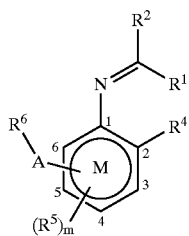

(I)

wherein $R^1$ and $R^2$, which may be the same or different, are chosen from among alkyl, acyl, cyano, alkoxycarbonyl, aminocarbonyl, alkenyl, alkynyl, carbocyclyl, heterocyclyl, each of which may be substituted, and hydrogen; or $R^2$ and $R^1$, together with their interconnecting atoms may form a ring, which may be substituted;

$R^4$ is chosen from among alkyl, alkenyl, alkynyl, carbocyclyl, heterocyclyl, each of which may be substituted; hydroxy; mercapto; azido; nitro; halogen; cyano; acyl; optionally substituted amino; cyanato; thiocyanato; —$SF_5$; —$OR^a$; —$SR^a$ and —$Si(R^a)_3$, where $R^a$ is alkyl, alkenyl, alkynyl, acyl, carbocyclyl or heterocyclyl, each of which may be substituted;

m is 0 to 3;

when present $R^5$, which may be the same or different to any other $R^5$, is any group defined for $R^4$;

$R^6$ is optionally substituted carbo- or heterocyclyl; and

A is a direct bond, —O—, —S(O)$_n$—, —NR$^9$—, —CR$^7$=CR$^7$—, —C≡C—, -A$^1$-, -A$^1$-A$^1$-, —O—(A$^1$)$_k$—O—, —O—(A$^1$)$_k$-, -A$^3$-, -A$^4$-, -A$^1$O—, -A$^1$S(O)$_n$—, -A$^2$-, —OA$^2$-, —NR$^9$A$^2$-, —OA$^2$-A$^1$-, —OA$^2$—C(R$^7$)=C(R$^8$)—, —S(O)$_n$A$^1$-, -A$^1$-A$^4$-, -A$^1$-A$^4$-C(R$^8$)=N—N=CR$^8$—, -A$^1$-A$^4$—C(R$^8$)=N—X$^2$—X$^3$—, -A$^1$-A$^4$-A$^3$-, -A$^1$-A$^4$-N(R$^9$)—, -A$^1$-A$^4$—X—CH$_2$—, -A$^1$-A$^4$-A$^1$-, -A$^1$-A$^4$-CH$_2$X—, -A$^1$-A$^4$-C(R$^8$)=N—X$^2$X$^3$—X$^1$—, -A$^1$-X—C(R$^8$)=N—, -A$^1$-X—C(R$^8$)=N—N=CR$^8$—, -A$^1$-X—C(R$^8$)=N—N(R$^9$)—, -A$^1$-X-A$^2$-X$^1$—, -A$^1$-O-A$^3$-, -A$^1$-O—C(R$^7$)=C(R$^9$)—, -A$^1$-O—N(R$^9$)-A$^2$-N(R$^9$)—, -A$^1$-O—N(R$^9$)-A$^2$-, -A$^1$-N(R$^9$)-A$^2$-N(R$^9$)—, -A$^1$-N(R$^9$)-A$^2$-, -A$^1$-N(R$^9$)—N=C(R$^8$)—, -A$^3$-A$^1$-, -A$^4$-A$^3$-, -A$^2$-NR$^9$—, -A$^1$-A$^2$-X$^1$—, -A$^1$-A$^1$-A$^2$-X$^1$—, —O-A$^2$-N(R$^9$)-A$^2$-, —CR$^7$=CR$^7$-A$^2$-X$^1$—, —C=C-A$^2$-X$^1$—, —N=C(R$^8$)-A$^2$-X$^1$—, —C(R$^8$)=N—N=C(R$^8$)—, —C(R$^8$)=N—N(R$^9$)—, —(CH$_2$)$_2$—O—N=C(R$^8$)-ou-X-A$^2$-N(R$^9$)— where:

n is 0, 1 or 2,
k is 1 to 9,
$A^1$ is —CHR$^7$—,
$A^2$ is —C(=X)—,
$A^3$ is —C(R$^8$)=N—O—,
$A^4$ is —O—N=C(R$^8$)—,
X is O or S,
$X^1$ is O, S, NR$^9$ or a direct bond,
$X^2$ is O, NR9 or a direct bond,
$X^3$ is hydrogen, —C(=O)—, —SO$_2$— or a direct bond, $R^7$, which may be the same or different to any other $R^7$, is alkyl, alkenyl, alkynyl, cyano, acyl, hydroxy, alkoxy, haloalkoxy, alkylthio, cycloalkyl or phenyl, each of which may be substituted; or is hydrogen or halogen;

$R^8$, which may be the same or different to any other $R^8$, is alkyl, alkenyl, alkynyl, alkoxy, alkylthio, carbo- or hetero-cyclyl, each of which may be substituted; or is hydrogen;

$R^9$, which may be the same or different to any other $R^9$, is optionally substituted alkyl, optionally substituted carbo- or hetero-cyclyl, hydrogen or acyl; or two $R^9$ groups on A, together with the connecting atoms, form a 5 to 7 membered ring;

where the moiety depicted on the right side of linkage A is attached to $R^6$; or -A-$R^6$ and $R^5$ together with benzene ring M form an optionally substituted fused ring system.

Preferably $R^1$ is alkyl, alkenyl or alkynyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or halogen), or is hydrogen or cyano. $R^1$ is especially $C_1$–$C_{10}$ alkyl (e.g. methyl) or hydrogen.

Preferably $R^2$ is alkyl, acyl, alkoxycarbonyl, aminocarbonyl, alkenyl or alkynyl, each of which may be substituted by alkoxy, haloalkoxy, alkylthio, halogen or optionally substituted phenyl (preferably phenyl, optionally substituted by alkyl, haloalkyl, alkoxy, haloalkoxy or alkylthio, each containing 1 to 5 carbon atoms, or by halogen), or is hydrogen, cyano or alkylcarbonyl. $R^2$ is especially $C_1$–$C_{10}$ alkyl (e.g. methyl or ethyl) or hydrogen.

Preferably $R^4$ is alkyl, alkenyl, or alkynyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or halogen); or is hydroxy; halogen; cyano; acyl (preferably —C(=O)R$^c$, —C(=S)R$^c$ or —S(O)$_p$R$^c$, where R$^c$ is alkyl, haloalkyl, alkoxy, haloalkoxy, alkylthio, amino, monoalkylamino, dialkylamino or phenyl optionally substituted by alkyl, haloalkyl, alkoxy, haloalkoxy or alkylthio; or phenyloxy, phenylthio, carbocyclyl, heterocyclyl); alkoxy; haloalkoxy; or alkylthio. R$^4$ is especially C$_1$–C$_{10}$ alkyl (e.g. methyl or ethyl) or halogen.

Preferably m is 0 or 1, especially 1.

When present, R$^5$ is preferably a group defined for preferred R$^4$ above. R$^5$ is especially C$_1$–C$_{10}$ alkyl or halogen.

When present, the group R$^5$ is preferably attached at the 5 position of ring M.

Preferably A is a direct bond, —O—, -A$^1$-, —S(O)$_n$A$^1$—, —O(A$^1$)$_k$—, —S(O)$_n$—, —NR$^9$A$^2$-, -A$^2$—, —OA$^2$, —OA$^2$-A$^1$-, —NR$^9$— or —O(A$^1$)$_k$O—. Particularly A is a direct bond, —O—, —S—, —NR$^9$—, —CHR$^7$— or —O—CHR$^7$—. Especially A is a direct bond or —O—.

When present, R$^9$ is alkyl, alkenyl, or alkynyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or halogen); or is hydrogen (R$^9$ is especially C$_1$–C$_{10}$ alkyl or hydrogen).

When present, R$^7$ is alkyl, alkenyl, or alkynyl, each of which may be substituted by alkoxy, haloalkoxy, alkylthio, halogen or optionally substituted phenyl (preferably phenyl optionally substituted by alkyl, haloalkyl, alkoxy, haloalkoxy or alkylthio, each containing 1 to 5 carbon atoms, or by halogen); or is hydroxy; halogen; cyano; acyl; alkoxy; haloalkoxy; alkylthio; or hydrogen (R$^7$ is especially C$_1$–C$_{10}$ alkyl or hydrogen).

Preferably A is attached to the 4 position of benzene ring M.

Preferably R$^6$ is optionally substituted phenyl or optionally substituted aromatic heterocyclyl [preferably thiazolyl, isothiazolyl, thiadiazolyl (particularly 1,2,4-thiadiazolyl), pyridyl or pyrimidinyl].

When substituted, R$^6$ may be substituted by one or more substituents, which may be the same or different, and may be selected from the preferred list: alkyl, alkenyl, alkynyl, carbo- or heterocyclyl, each of which may be substituted; hydroxy; mercapto; azido; nitro; halogen; cyano; acyl; optionally substituted amino; cyanato; thiocyanato; —SF$_5$; —OR$^a$; —SR$^a$ and —Si(R$^a$)$_3$, where R$^a$ is alkyl, alkenyl, alkynyl, carbocyclyl or heterocyclyl, each of which may be substituted.

A preferred list of substituents on R$^6$ is: hydroxy; halogen; cyano; acyl (preferably —C(=O)R$^C$, —C(=S)R$^C$ or —S(O)$_p$R$^c$, where R$^c$ is alkyl, haloalkyl, alkoxy, haloalkoxy, alkylthio, amino, monalkylamino, dialkylamino or phenyl optionally substituted by alkyl, haloalkyl, alkoxy, haloalkoxy or alkylthio; or phenyloxy, phenylthio, carbocyclyl, or heterocyclyl); amino; alkylamino; dialkylamino; alkyl; haloalkyl; R$^a$O-alkyl; acyloxyalkyl; cyano-oxyalkyl; alkoxy; haloalkoxy; alkylthio; carbocyclyl (preferably cyclohexyl or cyclopentyl) optionally substituted by alkyl, haloalkyl, alkoxy, haloalkoxy or alkylthio; and benzyl optionally substituted by alkyl, haloalkyl, alkoxy, haloalkoxy or alkylthio.

In a preferred embodiment, the invention provides the use of a compound of general formula (I) and salts thereof as fungicides wherein:

R$^1$ is alkyl, alkenyl or alkynyl, each of which may be substituted by alkoxy, haloalkoxy, alkylthio, halogen or phenyl optionally substituted by alkyl, haloalkyl, alkoxy, haloalkoxy, alkylthio or halogen; or is hydrogen;

R$^2$ is as defined for R$^1$ in this embodiment, or is acyl, aminocarbonyl or alkylcarbonyl;

R$^4$ is alkyl, alkenyl or alkynyl, each of which may be substituted by alkoxy, haloalkoxy, alkylthio, halogen or phenyl optionally substituted by alkyl, haloalkyl, alkoxy, haloalkoxy, alkylthio or halogen; or is hydroxy; halogen; cyano; acyl (preferably —C(=O)R$^c$, —C(=S)R$^c$ or —S(O)$_p$R$^c$, where R$^c$ is alkyl, haloalkyl, alkoxy, haloalkoxy, alkylthio, amino, monoalkylamino, dialkylamino or phenyl optionally substituted by alkyl, haloalkyl, alkoxy, haloalkoxy or alkylthio; or phenyloxy, phenylthio, carbocyclyl, heterocyclyl);

m is 0 or 1;

when present, R$^5$ is a group defined for R$^4$ in this embodiment;

A is a direct bond, —O—, —S—, —NR$^9$—, —CHR$^7$—or —O—CHR$^7$—, wherein when present, R$^9$ is alkyl, alkenyl, or alkynyl, each of which may be substituted by alkoxy, haloalkoxy, alkylthio, halogen or phenyl optionally substituted by alkyl, haloalkyl, alkoxy, haloalkoxy, alkylthio, or halogen; or is hydrogen; and R$^7$ is a group defined for R$^9$ in this embodiment, or is hydroxy; halogen; cyano; acyl; alkoxy; haloalkoxy or alkylthio;

A is attached to the 4 position of benzene ring M; and

R$^6$ is phenyl or aromatic heterocyclyl, optionally substituted by one or more substituents, which may be the same or different, and may be selected from the list: hydroxy; halogen; cyano; acyl (preferably —C(=O)R$^c$, —C(=S)R$^c$ or —S(O)$_p$R$^c$, where R$^c$ is alkyl, haloalkyl, alkoxy, haloalkoxy, alkylthio, amino, monoalkylamino, dialkylamino or phenyl optionally substituted by alkyl, haloalkyl, alkoxy, haloalkoxy or alkylthio; or phenyloxy, phenylthio, carbocyclyl, heterocyclyl); amino; alkylamino; dialkylamino; alkyl; haloalkyl; R$^a$O-alkyl; acyloxyalkyl; cyano-oxyalkyl; alkoxy; haloalkoxy; alkylthio; carbocyclyl (preferably cyclohexyl or cyclopentyl) optionally substituted by alkyl, haloalkyl, alkoxy, haloalkoxy or alkylthio; and benzyl optionally substituted by alkyl, haloalkyl, alkoxy, haloalkoxy or alkylthio.

Any alkyl group may be straight or branched and is preferably of 1 to 10 carbon atoms, especially 1 to 7 and particularly 1 to 5 carbon atoms.

Any alkenyl or alkynyl group may be straight or branched and is preferably of 2 to 7 carbon atoms and may contain up to 3 double or triple bonds which may be conjugated, for example vinyl, allyl, butadienyl or propargyl.

Any carbocyclyl group may be saturated, unsaturated or aromatic, and contain 3 to 8 ring-atoms. Preferred saturated carbocyclyl groups are cyclopropyl, cyclopentyl or cyclohexyl. Preferred unsaturated carbocyclyl groups contain up to 3 double bonds. A preferred aromatic carbocyclyl group is phenyl. The term carbocylic should be similarly construed. In addition, the term carbocyclyl includes any fused combination of carbocyclyl groups, for example naphthyl, phenanthryl, indanyl and indenyl.

Any heterocyclyl group may be saturated, unsaturated or aromatic, and contain 3 to 7 ring-atoms up to 4 of which may be hetero-atoms such as nitrogen, oxygen and sulphur. Examples of heterocyclyl groups are furyl, thienyl, pyrrolyl, pyrrolinyl, pyrrolidinyl, imidazolyl, dioxolanyl, oxazolyl, thiazolyl, imidazolyl, imidazolinyl, imidazolidinyl, pyrazolyl, pyrazolinyl, pyrazolidinyl, isoxazolyl, isothiazolyl, oxadiazolyl, triazolyl, thiadiazolyl, pyranyl, pyridyl (and pyridyl N-oxide), piperidinyl, dioxanyl, morpholino, dithianyl, thiomorpholino, pyridazinyl, pyrimidinyl, pyrazinyl, piperazinyl, sulpholanyl, tetrazolyl, triazinyl, azepinyl, oxazepinyl, thiazepinyl, diazepinyl and thiazolinyl.

In addition, the term heterocyclyl includes fused heterocyclyl groups, for example benzimidazolyl, benzoxazolyl, imidazopyridinyl, benzoxazinyl, benzothiazinyl, oxazolopyridinyl, benzofuranyl, quinolinyl, quinazolinyl, quinoxalinyl, dihydroquinazolinyl, benzothiazolyl, phthalimido, benzofuranyl, benzodiazepinyl, indolyl and isoindolyl. The term heterocyclic should be similarly construed.

Any alkyl, alkenyl, alkynyl, carbocyclyl or heterocyclyl group, when substituted, may be substituted by one or more substituents, which may be the same or different, and may be selected from the list: hydroxy; mercapto; azido; nitro; halogen; cyano; acyl; alkoxycarbonyl; optionally substituted aminocarbonyl; optionally substituted amino; optionally substituted ammonio; optionally substituted carbocyclyl; optionally substituted heterocyclyl; cyanato; thiocyanato; —SF$_5$; —OR$^a$; —SR$^a$; —SOR$^a$; —SO$_2$R$^a$ and —Si(R$^a$)$_3$, where R$^a$ is alkyl, alkenyl, alkynyl, carbocyclyl or heterocyclyl, each of which may be substituted. In the case of any carbocyclyl or heterocyclyl group the list includes additionally: alkyl, alkenyl and alkynyl, each of which may be substituted. Preferred substituents on any alkyl, alkenyl or alkynyl group are alkoxy, haloalkoxy or alkylthio, each containing 1 to 5 carbon atoms; halogen; or optionally substituted phenyl. Preferred substituents on any carbocyclyl or heterocyclyl group are alkyl, haloalkyl, alkoxy, haloalkoxy or alkylthio, each containing 1 to 5 carbon atoms; halogen; or optionally substituted phenyl.

In the case of any alkyl group or any unsaturated ring-carbon in any carbocyclyl or heterocyclyl group the list includes a divalent group such as oxo or imino, which may be substituted by optionally substituted amino, R$^a$ or —OR$^a$ (where R$^a$ is as defined above). Preferred groups are oxo, imino, alkylimino, oximino, alkyloximino or hydrazono.

Any amino group, when substituted and where appropriate, may be substituted by one or two substituents which may be the same or different, selected from the list: optionally substituted alkyl, optionally substituted amino, —OR$^a$ (where R$^a$ is as defined above)alkyl, alkenyl, alkynyl, carbocyclyl, heterocyclyl and acyl groups. Alternatively two substituents together with the nitrogen to which they are attached may form a heterocyclyl group, preferably a 5 to 7-membered heterocyclyl group, which may be substituted and may contain other hetero atoms, for example morpholino, thiomorpholino or piperidinyl.

The term acyl includes the residues of sulphur and phosphorus-containing acids as well as carboxylic acids. Typically the residues are covered by the general formulae —C(=X$^a$)R$^b$, —S(O)$_p$R$^b$ and —P(=X$^a$)(OR$^a$)(OR$^a$), where appropriate X$^a$ is O or S, R$^b$ is as defined for R$^a$, OR$^a$, —SR$^a$, optionally substituted amino or acyl; and p is 1 or 2. Preferred groups are —C(=O)R$^c$, —C(=S)R$^c$, and —S(O)$_p$R$^c$ where R$^c$ is alkyl, C$_1$ to C$_5$ alkoxy, C$_1$ to C$_5$ alkylthio, phenyl, phenyloxy, phenylthio, carbocyclyl, heterocyclyl or amino, each of which may be substituted.

Complexes of compounds of the invention are usually formed from a salt of formula MAn or MAn$_2$, in which M is a metal cation, e.g. copper, manganese, cobalt, nickel, iron or zinc and An is an anion, e.g. chloride, nitrate or sulphate.

In cases where the compounds of the invention comprise a nitrogen atom which may be oxidised, N-oxides of such compounds are also part of the invention.

In cases where the compounds of the invention exist as the E and Z isomers, the invention includes individual isomers as well as mixtures thereof.

In cases where compounds of the invention exist as tautomeric isomers, the invention includes individual tautomers as well as mixtures thereof.

In cases where the compounds of the invention exist as optical isomers, the invention includes individual isomers as well as mixtures thereof, including the racemic mixture.

The compounds of the invention have activity as fungicides, especially against fungal diseases of plants, e.g. mildews and particularly cereal powdery mildew (*Erysiphe graminis*) and vine downy mildew (*Plasmopara viticola*), rice blast (*Pyricularia oryzae*), cereal eyespot (*Pseudocercosporella herpotrichoides*), rice sheath blight (*Pellicularia sasakii*), grey mould (*Botrytis cinerea*), damping off (*Rhizoctonia solani*), wheat brown rust (*Puccinia recondita*), late tomato or potato blight (*Phytophthora infestans*), apple scab (*Venturia inaequalis*), and glume blotch (*Leptosphaeria nodorum*). Other fungi against which the compounds may be active include other powdery mildews, other rusts, and other general pathogens of Deuteromycete, Ascomycete, Phycomycete and Basidomycete origin.

The invention thus also provides a method of combating fungi at a locus infested or liable to be infested therewith, which comprises applying to the locus a compound of formula I.

The invention also provides an agricultural composition comprising a compound of formula I in admixture with an agriculturally acceptable diluent or carrier.

The composition of the invention may of course include more than one compound of the invention.

In addition, the composition can comprise one or more additional active ingredients, for example compounds known to possess plant-growth regulant, herbicidal, fungicidal, insecticidal, acaricidal, antimicrobial or antibacterial properties. Alternatively the compound of the invention can be used in a simultaneous, sequential and/or alternative way with the other active ingredient(s).

The diluent or carrier in the composition of the invention can be a solid or a liquid optionally in association with a surface-active agent, for example a dispersing agent, emulsifying agent or wetting agent. Suitable surface-active agents include anionic compounds such as a carboxylate, for example a metal carboxylate of a long chain fatty acid; an N-acylsarcosinate; mono- or di-esters of phosphoric acid with fatty alcohol ethoxylates or alkyl phenol ethoxylates or salts of such esters; fatty alcohol sulphates such as sodium dodecyl sulphate, sodium octadecyl sulphate or sodium cetyl sulphate; ethoxylated fatty alcohol sulphates; ethoxylated alkylphenol sulphates; lignin sulphonates; petroleum sulphonates; alkyl-aryl sulphonates such as alkyl-benzene sulphonates or lower alkylnaphthalene sulphonates, e.g. butylnaphthalene sulphonate; salts of sulphonated naphthalene-formaldehyde condensates; salts of sulphonated phenol-formaldehyde condensates; or more complex sulphonates such as the amide sulphonates, e.g. the sulphonated condensation product of oleic acid and N-methyl taurine; the dialkyl sulphosuccinates, e.g. the sodium sulphonate of dioctyl succinate; acid derivatives of alkyl glycosides and alkylpolyglycosides materials and their metal salts, e.g. alkyl polyglycoside citrate or tartrate materials; or mono-, di- and tri-alkyl esters of citric acid and their metal salts.

Nonionic agents include condensation products of fatty acid esters, fatty alcohols, fatty acid amides or fatty-alkyl- or alkenyl-substituted phenols with ethylene and/or propylene oxide; fatty esters of polyhydric alcohol ethers, e.g. sorbitan fatty acid esters; condensation products of such esters with ethylene oxide, e.g. polyoxyethylene sorbitan fatty acid esters; alkyl glycosides, alkyl polyglycoside materials; block copolymers of ethylene oxide and propylene oxide; acetylenic glycols such as 2,4,7,9-tetramethyl-5-decyne-4,7-diol, ethoxylated acetylenic glycols; acrylic based graft copolymers; alkoxylated siloxane surfactants; or imidazoline type surfactants, e.g. 1-hydroxyethyl-2-alkylimidazoline.

Examples of a cationic surface-active agent include, for instance, an aliphatic mono-, di-, or polyamine as an acetate, naphthenate or oleate; an oxygen-containing amine such as an amine oxide, polyoxyethylene alkylamine or polyoxypropylene alkylamine; an amide-linked amine prepared by the condensation of a carboxylic acid with a di- or polyamine; or a quaternary ammonium salt.

The compositions of the invention can take any form known in the art for the formulation of agrochemicals, for example, a solution, an aerosol, a dispersion, an aqueous emulsion, a microemulsion, a dispersible concentrate, a dusting powder, a seed dressing, a fumigant, a smoke, a dispersible powder, an emulsifiable concentrate, granules or an impregnated strip. Moreover it can be in a suitable form for direct application or as a concentrate or primary composition which requires dilution with a suitable quantity of water or other diluent before application.

A dispersible concentrate comprises a compound of the invention dissolved in one or more water miscible or semi-water miscible solvents together with one or more surface active and/or polymeric material. Addition of the formulation to water results in the crystallisation of the active ingredient, the process being controlled by the surfactants and/or polymers resulting in a fine dispersion.

A dusting powder comprises a compound of the invention intimately mixed and ground with a solid pulverulent diluent, for example, kaolin.

An emulsifiable concentrate comprises a compound of the invention dissolved in a water-immiscible solvent which forms an emulsion or microemulsion on addition to water in the presence of an emulsifying agent.

A granular solid comprises a compound of the invention associated with similar diluents to those that may be employed in dusting powders, but the mixture is granulated by known methods. Alternatively it comprises the active ingredient absorbed or coated on a pre-formed granular carrier, for example, Fuller's earth, attapulgite, silica or limestone grit.

Wettable powders, granules or grains usually comprise the active ingredient in admixture with suitable surfactants and an inert powder diluent such as clay or diatomaceous earth.

Another suitable concentrate is a flowable suspension concentrate which is formed by grinding the compound with water or other liquid, surfactants and a suspending agent.

The concentration of the active ingredient in the composition of the present invention, as applied to plants is preferably within the range of 0.0001 to 1.0 per cent by weight, especially 0.0001 to 0.01 per cent by weight. In a primary composition, the amount of active ingredient can vary widely and can be, for example, from 5 to 95 per cent by weight of the composition.

In use a compound of the invention is generally applied to seeds, plants or their habitat. Thus, the compound can be applied directly to the soil before, at or after drilling so that the presence of active compound in the soil can control the growth of fungi which may attack seeds. When the soil is treated directly the active compound can be applied in any manner which allows it to be intimately mixed with the soil such as by spraying, by broadcasting a solid form of granules, or by applying the active ingredient at the same time as drilling by inserting it in the same drill as the seeds. A suitable application rate is within the range of from 5 to 1000 g per hectare, more preferably from 10 to 500 g per hectare.

Alternatively the active compound can be applied directly to the plant by, for example, spraying or dusting either at the time when the fungus has begun to appear on the plant or before the appearance of fungus as a protective measure. In both such cases the preferred mode of application is by foliar spraying. It is generally important to obtain good control of fungi in the early stages of plant growth, as this is the time when the plant can be most severely damaged. The spray or dust can conveniently contain a pre- or post-emergence herbicide if this is thought necessary. Sometimes, it is practicable to treat the roots, bulbs, tubers or other vegetative propagule of a plant before or during planting, for example, by dipping the roots in a suitable liquid or solid composition. When the active compound is applied directly to the plant a suitable rate of application is from 0.025 to 5 kg per hectare, preferably from 0.05 to 1 kg per hectare.

In addition, the compounds of the invention can be applied to harvested fruits, vegetables or seeds to prevent infection during storage.

In addition, the compounds of the invention can be applied to plants or parts thereof which have been genetically modified to exhibit a trait such as fungal and/or herbicidal resistance.

In addition the compounds of the invention can be used to treat fungal infestations in timber and in public health applications. Also the compounds of the invention can be used to treat fungal infestations in domestic and farm animals.

Compounds of the invention may be prepared, in known manner, in a variety of ways.

Compounds of general formula I may be prepared from compounds of general formula II which are reacted with $R^1$—CO—$R^2$ according to Scheme 1. Such reactant can be obtained from commercial suppliers or prepared by methods apparent to the skilled in the art. As a general manner, all starting materials used for the preparation of the compounds of the invention are either commercially available or can be prepared by well-known method from the skilled in the art. Such methods can for example be found in the literature, in patents, in the "Chemical Abstracts", in electronic databases or on the Internet.

Scheme 1

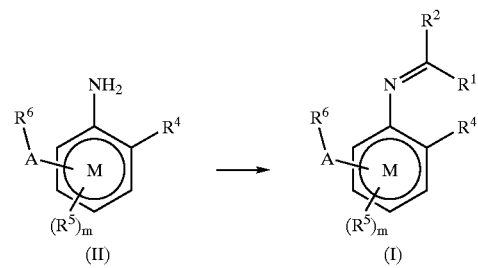

Such reaction is well known from the one skilled in the art and can be conducted according general references such as J. March, *Advanced Organic Chemistry*, IV edition, pages 1289 sqq.

Compounds of formula I can be thus prepared, for example, by combination of the following reactants listed in table A (compounds of formula II) and table B (compounds of formula $R^1$—CO—$R^2$) below:

TABLE A

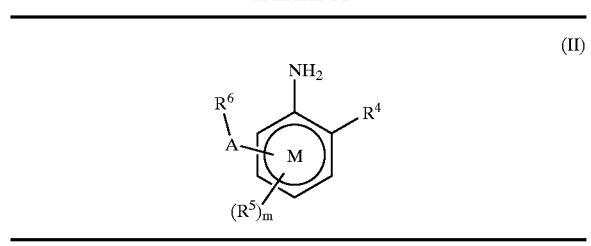
(II)

A1 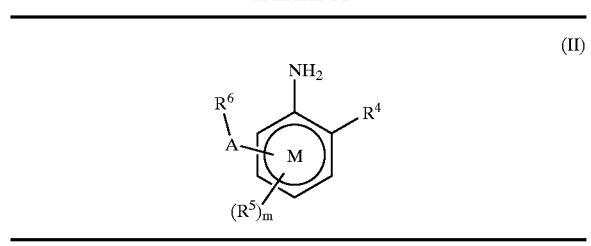

A2 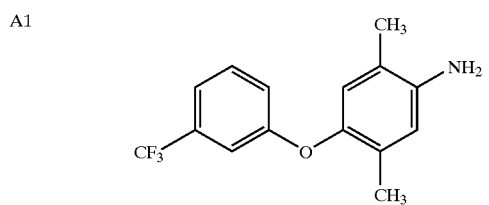

A3 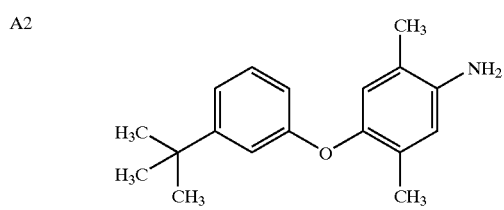

A4 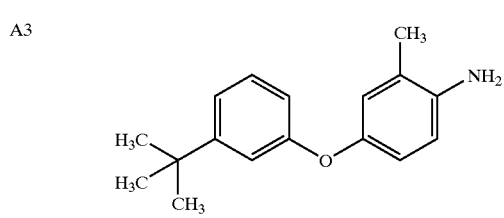

A5 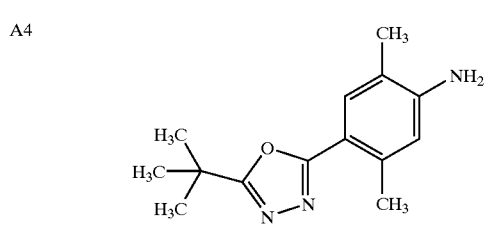

A6 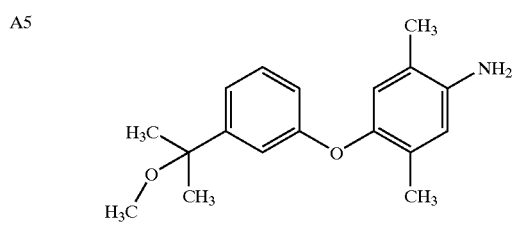

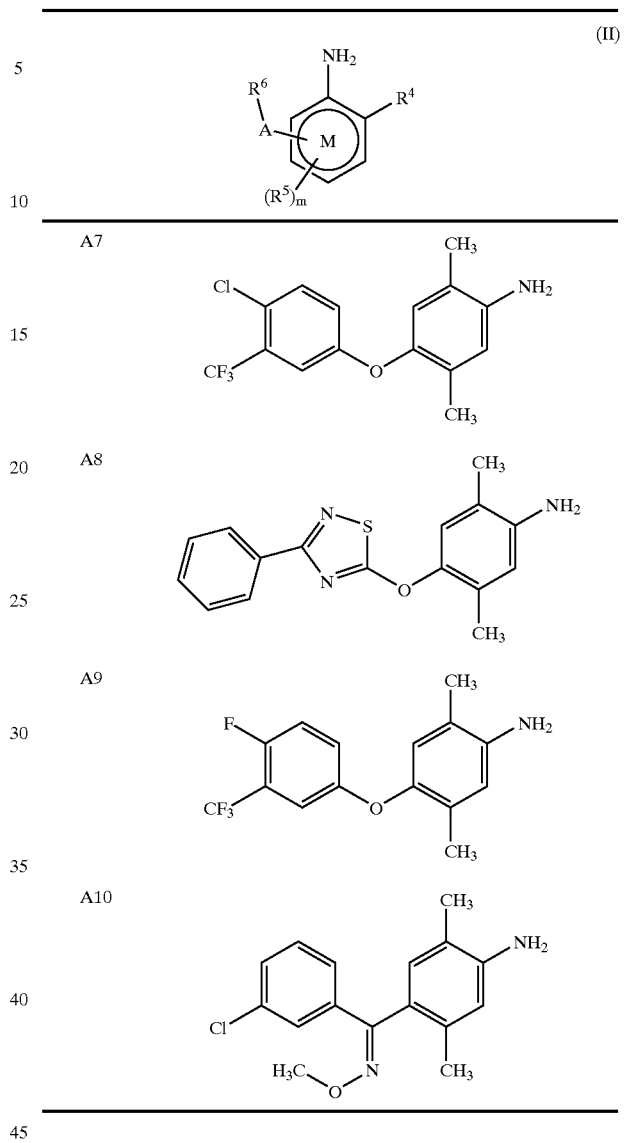

| | $R^1$ | $R^2$ |
|---|---|---|
| B1 | H | H |
| B2 | H | Cyclopropyl |
| B3 | H | 2-thiazolyl |
| B4 | H | 4-pyridinyl-N-oxide |
| B5 | H | Methylthioethyl |
| B6 | H | Trimethylammoniomethyl |
| B7 | H | 2-pyridyl |
| B8 | H | 1-methyl-2-pyrrolyl |
| B9 | H | Isopropyl |
| B10 | H | 5-nitro-2-furyl |
| B11 | H | 4-dimethylaminophenyl |
| B12 | H | Ethylaminoethyl |
| B13 | H | 2-methoxyvinyl |
| B14 | H | Trifluoromethyl |
| B15 | H | Phenyl |
| B16 | H | Methyl |
| B17 | Methyl | 2-pyridyl |
| B18 | Methyl | Ethylaminoethyl |
| B19 | Methyl | 2-methoxyvinyl |

TABLE B-continued

| | $R^1$-CO-$R^2$ | |
|---|---|---|
| | $R^1$ | $R^2$ |
| B20 | Methyl | Trifluoromethyl |
| B21 | Methyl | Cyclopropyl |
| B22 | Methyl | 2-thiazolyl |
| B23 | Methyl | 4-pyridinyl-N-oxide |
| B24 | Methyl | Methylthioethyl |
| B25 | Methyl | Trimethylammoniomethyl |
| B26 | Methyl | 1-methyl-2-pyrrolyl |
| B27 | Methyl | Isopropyl |
| B28 | Methyl | 5-nitro-2-furyl |
| B29 | Methyl | 4-dimethylaminophenyl |
| B30 | Methyl | Phenyl |
| B31 | Phenyl | Phenyl |
| B32 | Phenyl | 2-pyridyl |
| B33 | Phenyl | Ethylaminoethyl |
| B34 | Phenyl | 2-methoxyvinyl |
| B35 | Phenyl | Trifluoromethyl |
| B36 | Phenyl | Cyclopropyl |
| B37 | Phenyl | 2-thiazolyl |
| B38 | Phenyl | 4-pyridinyl-N-oxide |
| B39 | Phenyl | Methylthioethyl |
| B40 | Phenyl | Trimethylammoniomethyl |
| B41 | Phenyl | 1-methyl-2-pyrrolyl |
| B42 | Phenyl | Isopropyl |
| B43 | Phenyl | 5-nitro-2-furyl |
| B44 | Phenyl | 4-dimethylaminophenyl |

Compounds of general formula II may be prepared by reduction of the nitro group in compounds of formula III according to reaction scheme 2. Preferred reaction conditions comprise reaction with stannous chloride in concentrated hydrochloric acid.

Scheme 2

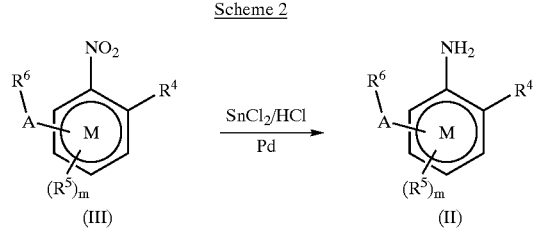

(III) → (II)

Compounds of formula IIa, i.e. compounds of general formula II where A is a direct bond, may be prepared according to reaction scheme 3, where $X^v$ is a leaving group.

Scheme 3

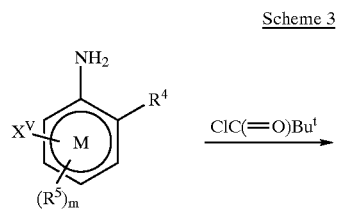

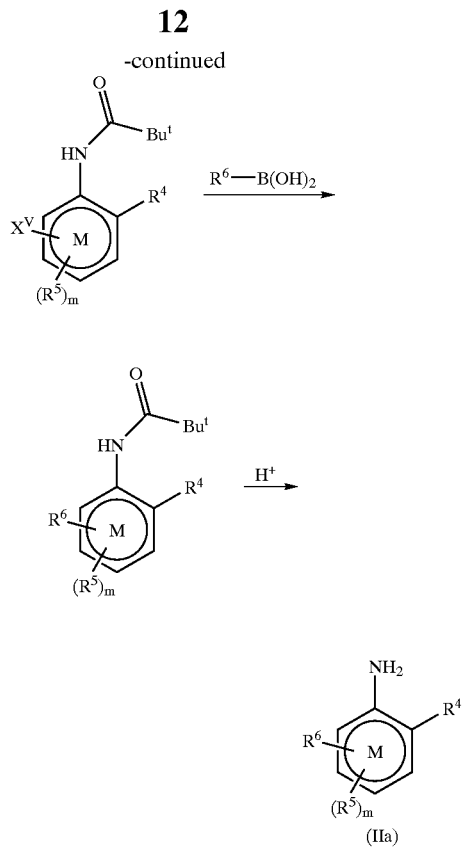

(IIa)

Compounds of formula IIb, i.e. compounds of general formula II where $R^4$ is halogen, may be prepared according to scheme 4 where $X^T$ represents halogen. When $R^4$ is bromine preferred reaction conditions comprise stirring with bromine in a suitable solvent.

Scheme 4

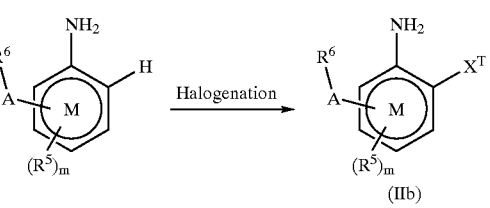

(IIb)

Compounds of formula IIc, i.e. compounds of general formula II where A is NHC(=O)—; compounds of formula IId, i.e. compounds of formula II where A is a direct bond and $R^6$ is optionally substituted phthalimido, where the curved line connecting the 3 and 4 positions of the phthalimido group represents the optionally substituted carbocyclic ring; and compounds of formula IIe, i.e. compounds of general formula II where A is a direct bond and $R^6$ is pyrrolyl, optionally substituted at the 2 and 5 positions by one or more groups R which may be the same or different; may be prepared from compounds of formula IV according to methodology shown in reaction scheme 5. For certain compounds of formula IV, protection/deprotection of the amino group ortho to $R^4$ may be required to improve yields.

Scheme 5

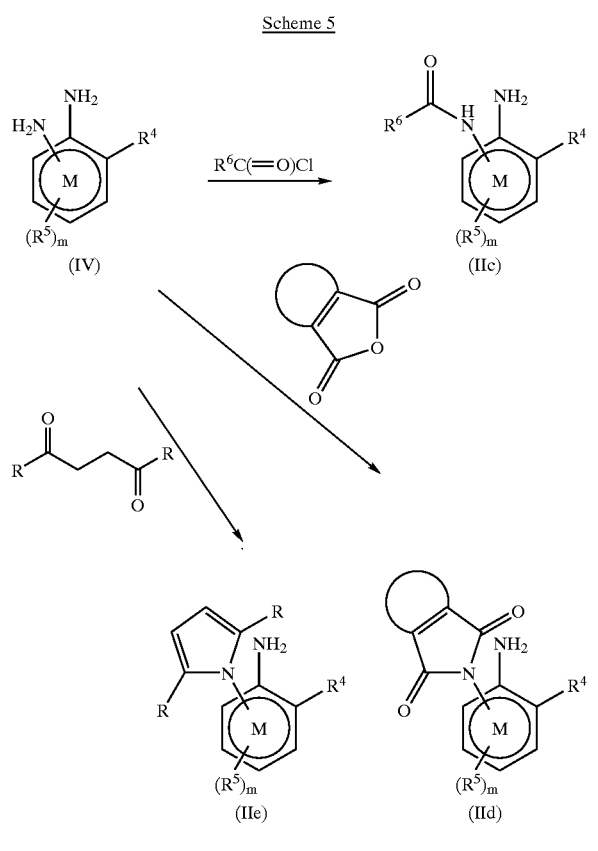

Compounds of formula IIIa, i.e. compounds of general formula III where A is a group $A^z$, may be prepared by reacting compounds of formula V with compounds of formula VI according to reaction scheme 6. $A^z$ is a group which, in compound V, forms an anion under basic conditions. $A^z$ is alternatively a basic primary or secondary nitrogen atom. $X^z$ is a leaving group, preferably halogen. When $A^z$ is oxygen, preferred reaction conditions comprise treating V with sodium hydride followed by addition of VI. When $A^z$ is sulphur preferred reaction conditions comprise reacting V with VI in the presence of a tertiary amine base such as ethyldiisopropylamine. When $A^z$ is —CHR$^7$—, preferred reaction conditions comprise treating V with potassium tert-butoxide in dimethylformamide at low temperature. When $A^z$ is a basic nitrogen atom, no base is required.

Scheme 6

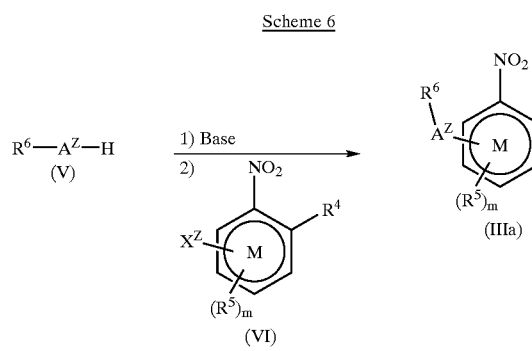

Compounds of formula IIIb, i.e. compounds of general formula III where A is a group $A^w$, may be prepared by reacting compounds of formula VII with compounds of formula VIII according to reaction scheme 7. $A^w$ is a group which, in compound VII, forms an anion under basic conditions. $X^w$ is a leaving group, preferably halogen. Preferred basic conditions comprise reaction of VII with potassium carbonate or sodium hydride followed by addition of VIII.

Scheme 7

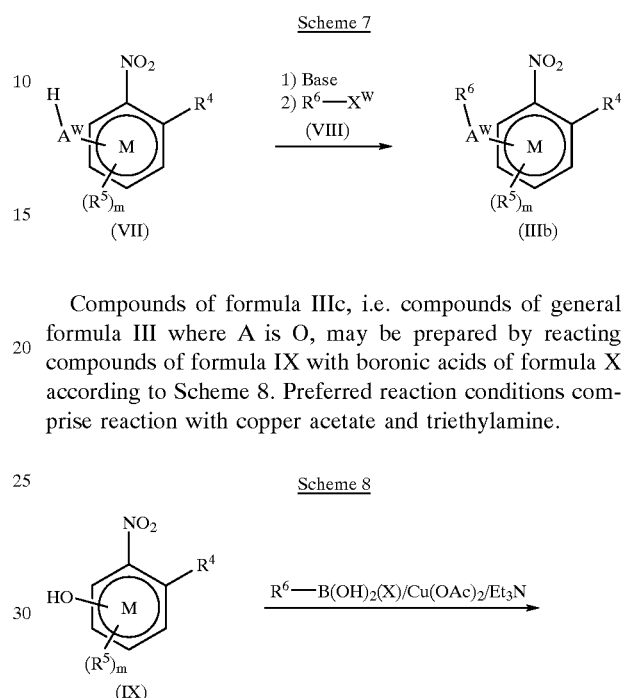

Compounds of formula IIIc, i.e. compounds of general formula III where A is O, may be prepared by reacting compounds of formula IX with boronic acids of formula X according to Scheme 8. Preferred reaction conditions comprise reaction with copper acetate and triethylamine.

Scheme 8

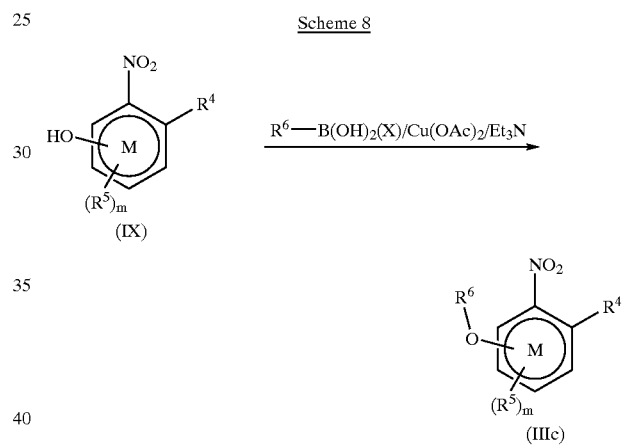

Compounds of formula IIId, i.e. compounds of formula III where A is a direct bond may be prepared according to reaction scheme 9 from compounds of formula XI where $X^z$ is a leaving group, preferably halogen.

Scheme 9

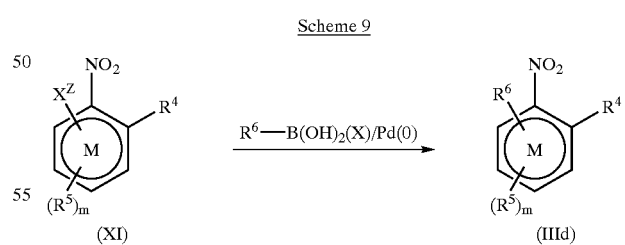

Compounds of formula III where A is a direct bond and $R^6$ is a heterocyclyl can be prepared using a variety of methods known to a skilled chemist (for example see "Comprehensive Heterocyclic Chemistry", Vols 1–7, A. R. Katritzky and C. W. 20 Rees). By way of example, routes to compounds of formula III containing a 1,2,4-oxadiazol-3-yl group (compound IIIe) and a 1,3,4-oxadiazol-2-yl group (compound IIIf) are shown in schemes 10 and 11.

Scheme 10

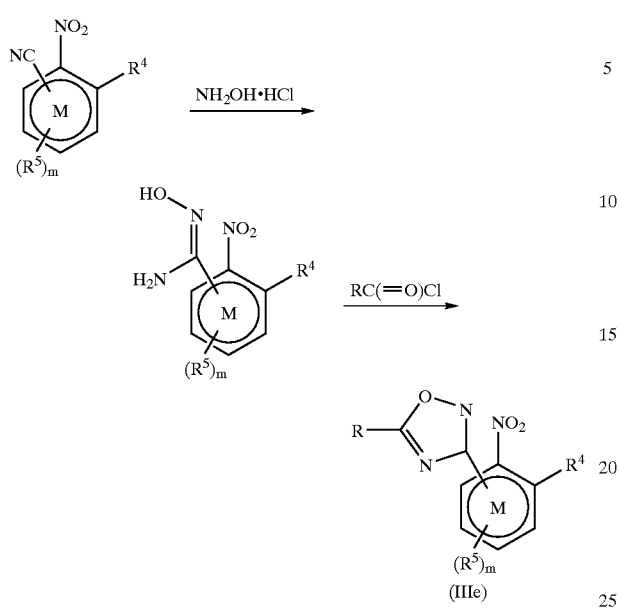

Scheme 11

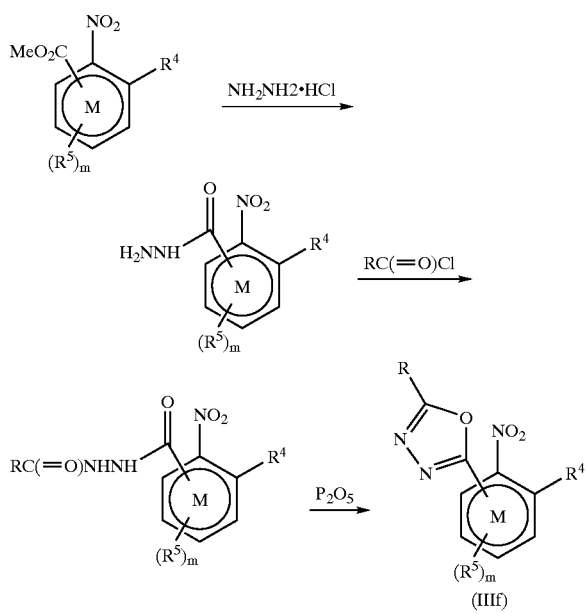

Alternatively, using similar chemistry to that described above, compounds of formula I can be prepared by introducing $R^6$ after formation of the imine moiety.

Other methods will be apparent to the chemist skilled in the art, as will be methods for preparing starting materials and intermediates.

In addition, compounds of the invention may be prepared using combinatorial chemistry methodology.

The invention is illustrated in the following Examples. Structures of isolated, novel compounds were confirmed by N.M.R., mass spectrometry and/or other appropriate analyses. Proton N.M.R. spectra ($^1$H N.M.R.) were determined in deuterochloroform and chemical shifts (δ) are quoted in parts per million downfield of tetramethylsilane.

EXAMPLE 1

Preparation of Compound 5 (see table 1 below)

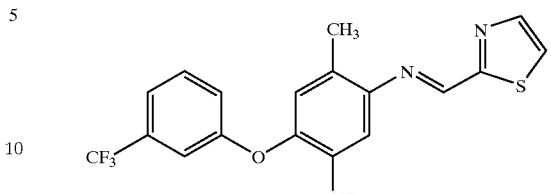

Step 1: Preparation of 2-nitro-5-(3-trifluoromethylphenoxy)-p-xylene

To a suspension of sodium hydride (0.4 g of 60% in oil) in dry N-methylpyrroli-dinone (10 ml) was slowly added 3-trifluoromethylphenol (1.62 g). When effervescence had ceased, 3-chloro-6-nitro-p-xylene (1.85 g) was added and the mixture stirred at 120–40° C. for 5 hours. On cooling, the mixture was poured into water and the mixture extracted with diethyl ether (x3). The combined ether extracts were dried (MgSO$_4$), filtered and evaporated to give the title compound as a solid, m.p. 68–71° C.

Step 2: Preparation of 4-(3-trifluoromethylphenoxy)-2,5-xylidine (Compound A1, Table A)

To a stirred mixture of stannous chloride (10.8 g) in concentrated hydrochloric acid (24 ml) and ethanol (50 ml) was added the product from Step 1 above (2.46 g) and the mixture was heated at 75° C. for 2 hours. On cooling potassium hydroxide solution was added slowly with cooling. The mixture was extracted with diethyl ether (x3) and the combined extracts were washed with brine, dried (MgSO$_4$), filtered and evaporated to dryness to give a crude residue which was purified by silica gel chromatography eluting with light petroleum (b.p.60–80° C.)/ethyl acetate (3:1) to give the title product, m.p. 58–60° C.

Step 3: Preparation of:

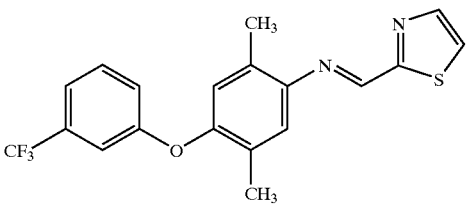

To the aniline A1 obtained from Step 2 (0.178 g) and 2-thiazolylcarbaldehyde (compound B3, Table B) (0.0717 g) dissolved in toluene (20 ml) was added anhydrous magnesium sulphate (0.2 g) and the reaction stirred at ambient temperature for 20 hours. The magnesium sulphate was filtered with toluene and the organic solvent was removed under reduced pressure to afford the title compound.

Mass spectroscopy analysis: 377 (M+H).

EXAMPLE 2

Preparation of Compound 16 (see table 1 below)

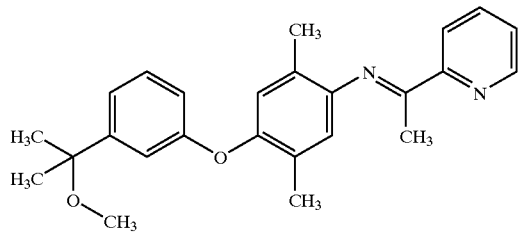

The aniline A5 (Table A) (0.18g) and the ketone B17 (Table B) (0.0758g) were refluxed for 20 hours in toluene (30ml) containing a catalytic amount of p-toluene sulphonic acid, collecting water by azeotropic distillation. The solution was cooled, washed with saturated sodium hydrogenocarbonate, dried over magnesium sulphate and solvent removed under reduced pressure. Purification by HPLC afforded the title compound.

Mass spectroscopy analysis: 389 (M+H).

The following compounds of formula Ia (see Table 1), i.e. compounds of general formula I where -A-$R^6$ is para to the imine moiety, may be prepared by methods analogous to those of Examples 1 and 2.

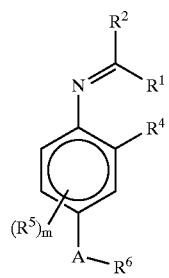

TABLE 1

| Cmpd | R1 | R2 | R4 | R5 | A | R6 | MS result |
|---|---|---|---|---|---|---|---|
| 1 | Phenyl | H | Me | 5-Me | O | 2-benzyloxyphenyl | |
| 2 | 2-thiazolyl | H | Me | 5-Me | O | 3-trifluoromethyl-4-chlorophenyl | 411 (M + H) |
| 3 | 2-thiazolyl | H | Me | 5-Me | O | 3-t-butylphenyl | 365 (M + H) |
| 4 | 2-thiazolyl | H | Me | 5-Me | O | 3-trifluoromethyl-4-fluorophenyl | 395 (M + H) |
| 5 | 2-thiazolyl | H | Me | 5-Me | O | 3-trifluoromethylphenyl | 377 (M + H) |
| 6 | 2-thiazolyl | H | Me | 5-Me | O | 3-chlorophenyl | 343 (M + H) |
| 7 | N-methyl-2-pyrrolyl | H | Me | 5-Me | O | 3-trifluoromethyl-4-chlorophenyl | 407 (M + H) |
| 8 | 2-nitro-5-furanyl | H | Me | 5-Me | O | 3-trifluoromethyl-4-fluorophenyl | 423 (M + H) |
| 9 | 2-nitro-5-furanyl | H | Me | 5-Me | O | 3-(1-methoxy-1-methylethyl)phenyl | 409 (M + H) |
| 10 | 4-dimethylaminophenyl | H | Me | 5-Me | O | 3-trifluoromethyl-4-fluorophenyl | 431 (M + H) |
| 11 | 2-nitro-5-furanyl | H | Me | 5-Me | O | 3-trifluoromethyl-4-Chlorophenyl | 439 (M + H) |
| 12 | 4-dimethylaminophenyl | H | Me | 5-Me | O | 3-trifluoromethyl-4-chlorophenyl | 447 (M + H) |
| 13 | 4-dimethylaminophenyl | H | Me | 5-Me | O | 3-t-butylphenyl | 401 (M + H) |
| 14 | N-methyl-2-pyrrolyl | H | Me | 5-Me | O | 3-(1-methoxy-1-methylethyl)phenyl | 377 (M + H) |
| 15 | N-methyl-2-pyrrolyl | H | Me | 5-Me | O | 3-trifluoromethylphenyl | 373 (M + H) |
| 16 | 2-pyridyl | Me | Me | 5-Me | O | 3-(1-methoxy-1-methylethyl)phenyl | 389 (M + H) |

Test Examples

Compounds were assessed for activity against one or more of the following phytopathogenic diseases:

*Erysiphe graminis f. sp. tritici*: wheat powdery mildew

*Puccinia recondita*: wheat brown rust

*Septoria nodorum*: wheat septoria nodorum

*Septoria tritici*: wheat septoria tritici

*Pyrenophora teres*: barley net blotch

Aqueous solutions or dispersions of the compounds of the invention at the desired concentration, including one or more wetting agents, were applied by spray or by drenching the stem base of the test plants, as appropriate. After a given time, plants or plant parts were inoculated with appropriate test pathogens and kept under controlled environmental conditions suitable for maintaining plant growth and development of the disease. After an appropriate time, the degree of infection of the affected part of the plant was visually estimated. At a concentration of 500 ppm (w/v) or less, the following compounds present a control of at least 65% on the specified fingal diseases versus non-treated test.

*Pyricularia grisea*: 2, 3, 4, 5, 6

*Pvricularia grisea*: 2, 3, 4, 5

*Fusarium culmorum*: 2

*Septoria tritici*: 4, 5

*Pythium ultimum*: 4.

What is claimed is:

1. A compound of general formula I and salts thereof as fungicides

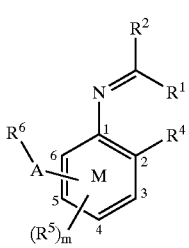

wherein $R^1$ and $R^2$ are independently selected from the group consisting of alkyl, carbocyclyl, heterocyclyl, each of which may be substituted, and hydrogen;

$R^4$ is selected from the group consisting of alkyl, hydroxy, and halogen;

m is 0 to 3;

when present $R^5$, which may be the same or different from to any other $R^5$, is any group defined for $R^4$;

$R^6$ is optionally substituted carbo- or heterocyclyl; and

A is a direct bond or —O—.

2. A compound according to claim 1 wherein $R^1$ is alkyl, which may be substituted; or is hydrogen.

3. A compound according to claim 1 wherein $R^1$ is $C_1$–$C_{10}$ alkyl or hydrogen.

4. A compound according to claim 1 wherein $R^1$ is methyl or hydrogen.

5. A compound according to claim 1 wherein $R^2$ is alkyl, which may be substituted or is hydrogen.

6. A compound according to claim 1 wherein $R^2$ is C–$C_{10}$ alkyl or hydrogen.

7. A compound according to claim 1 wherein $R^2$ is methyl or hydrogen.

8. A compound according to claim 1 wherein $R^4$ is alkyl, which may be substituted; or is hydroxy; halogen.

9. A compound according to claim 1 wherein $R^4$ is $C_1$–$C_{10}$ alkyl or halogen.

10. A compound according to claim 1 wherein $R^4$ is methyl or ethyl or halogen.

11. A compound according to claim 1 wherein m is 0 or 1.

12. A compound according to claim 1 wherein $R^5$ is attached at the 5 position of ring M.

13. A compound according to claim 1 wherein A is attached to the 4 position of benzene ring M.

14. A compound according to claim 1 wherein $R^6$ is optionally substituted aromatic heterocyclyl.

15. A compound according to claim 1 wherein $R^6$ is optionally substituted thiazolyl, isothiazolyl, thiadiazolyl, pyridyl or pyrimidinyl.

16. A compound according to claim 1 wherein $R^6$ is optionally substituted 1,2,4-thiadiazolyl.

17. A compound according to claim 1 wherein $R^6$ may be substituted by one or more substituents independently selected from the group consisting of alkyl, alkenyl, alkynyl, carbo- or heterocyclyl, each of which may be substituted; hydroxy; mercapto; azido; nitro; halogen; cyano; acyl; optionally substituted amino; cyanato; thiocyanato; —SF, —$OR^a$; —$SR^a$ and —$Si(R^a)$, where $R^a$ is alkyl, alkenyl, alkynyl, carbocyclyl or heterocyclyl, each of which may be substituted.

18. A compound according to claim 17 wherein $R^6$ may be substituted by one or more substituents independently selected from the group consisting of hydroxy; halogen; cyano; acyl; amino; alkylamino; dialkylamino; alkyl; haloalkyl; $R^aO$—alkyl; acyloxyalkyl; cyano-oxyalkyl; alkoxy; haloalkoxy; alkylthio; carbocyclyl, optionally substituted by alkyl, haloalkyl, alkoxy, haloalkoxy or alkylthio; and benzyl optionally substituted by alkyl, haloalkyl, alkoxy, haloalkoxy or alkylthio.

19. A fungicidal composition comprising at least one compound as claimed in claim 1 in admixture with an agriculturally acceptable diluent or carrier.

20. A method of combating fungi at a locus infested or liable to be infested therewith, which comprises applying to the locus a compound as claimed in claim 1.

* * * * *

UNITED STATES PATENT AND TRADEMARK OFFICE
CERTIFICATE OF CORRECTION

PATENT NO. : 6,933,307 B2
DATED : August 23, 2005
INVENTOR(S) : Gerusz et al.

It is certified that error appears in the above-identified patent and that said Letters Patent is hereby corrected as shown below:

<u>Title page,</u>
Item [75], Inventors, should read:
-- Vincent Gerusz, San Antonio, Texas (US)
  Darren James Mansfield, Lyon (FR)
  Joseph Perez, Lyon (FR)
  Jean-Pierre Vors, Lyon (FR) --.

Signed and Sealed this

Thirtieth Day of May, 2006

JON W. DUDAS
*Director of the United States Patent and Trademark Office*